US009090877B2

(12) United States Patent
Piccirilli

(10) Patent No.: US 9,090,877 B2
(45) Date of Patent: Jul. 28, 2015

(54) METHOD FOR OBTAINING ALGAE EXTRACTS AND USE OF THESE EXTRACTS

(75) Inventor: Antoine Piccirilli, Poitiers (FR)

(73) Assignee: VALAGRO CARBONE RENOUVELABLE POITOU-CHARENTES, Poitiers (FR)

( * ) Notice: Subject to any disclaimer, the term of this patent is extended or adjusted under 35 U.S.C. 154(b) by 1233 days.

(21) Appl. No.: 13/003,977

(22) PCT Filed: Jul. 17, 2009

(86) PCT No.: PCT/FR2009/051429
§ 371 (c)(1),
(2), (4) Date: Jan. 13, 2011

(87) PCT Pub. No.: WO2010/007328
PCT Pub. Date: Jan. 21, 2010

(65) Prior Publication Data
US 2011/0142875 A1 Jun. 16, 2011

(30) Foreign Application Priority Data

Jul. 18, 2008 (FR) ..................... 08 54908

(51) Int. Cl.
| | | |
|---|---|---|
| A01N 65/00 | (2009.01) | |
| C12N 1/06 | (2006.01) | |
| A61K 36/00 | (2006.01) | |
| A23K 1/14 | (2006.01) | |
| A23K 1/18 | (2006.01) | |
| A23L 1/337 | (2006.01) | |
| A61K 8/37 | (2006.01) | |
| A61K 8/97 | (2006.01) | |
| A61K 36/02 | (2006.01) | |
| A61Q 19/00 | (2006.01) | |
| C05F 11/10 | (2006.01) | |
| C05G 3/00 | (2006.01) | |
| C10L 1/02 | (2006.01) | |
| C12N 1/12 | (2006.01) | |

(52) U.S. Cl.
CPC . *C12N 1/066* (2013.01); *A23K 1/14* (2013.01); *A23K 1/188* (2013.01); *A23L 1/337* (2013.01); *A61K 8/37* (2013.01); *A61K 8/975* (2013.01); *A61K 36/00* (2013.01); *A61K 36/02* (2013.01); *A61Q 19/00* (2013.01); *C05F 11/10* (2013.01); *C05G 3/0064* (2013.01); *C10L 1/023* (2013.01); *C10L 1/026* (2013.01); *C12N 1/12* (2013.01); *Y02E 50/13* (2013.01)

(58) Field of Classification Search
CPC ............................... A61K 36/00; A61K 36/02
USPC ....................................................... 424/725
See application file for complete search history.

(56) References Cited

U.S. PATENT DOCUMENTS

| 4,646,633 A | 3/1987 | Falguieres |
| 5,951,875 A | 9/1999 | Kanel et al. |
| 6,180,845 B1 | 1/2001 | Catallo et al. |

FOREIGN PATENT DOCUMENTS

| CN | 1072083 A | | 5/1993 |
| CN | 1502273 | * | 6/2004 |
| CN | 1502273 A | | 6/2004 |
| CN | 101024647 A | | 8/2007 |
| FR | 2563704 A1 | | 11/1985 |
| FR | 2643632 A1 | | 8/1990 |
| GB | 319333 A | | 12/1930 |
| GB | 2150552 A | | 7/1985 |
| JP | 2007116963 | * | 5/2014 |

OTHER PUBLICATIONS

Best, G., "Alternative energy crops for agricultural machinery biofuels—focus on biodiesel", Agricultural Engineering International, vol. 8, Invited Overview 13, 2006.
Translation of Chinese Office Action dated May 7, 2012, from corresponding CN application.
Gouveia et al.: "Functional food oil coloured by pigments extracted from microalgae with supercritical CO2", Food Chemistry, Elsevier Science Publishers LTC, GB, vol. 101, No. 2, Sep. 2006, pp. 717-723, ISSN: 0308-8146.
Mendiola et al.: "Screening of functional compounds in supercritical fluid extracts from spirulina platensis", Food Chemistry, Elsevier Science Publishers, LTD, GB, vol. 102, No. 4, Jan. 31, 2007, pp. 1357-1367, ISSN: 0308-8146.
Nternational Search Report, dated Dec. 9, 2009, from corresponding PCT application.
Hammes, Frederik; et al. "Formation of assimilable organic carbon (AOC) and specific natural organic matter (NOM) fractions during ozonation of phytoplankton," Water Research 41 (2007) 1447-1454.
Lockhart, C.M.; et al. "Phytohaemagglutinins From the Nitrogen-Fixing Lichens Peltigera Canina and P. Polydactyla," FEMS Microbiology Letters 3 (1978) 127-130.
Peschek, Gunter A., et al. "Characterization of the Cytochrome c Oxidase in Isolated an Purified Plasma Membranes from the Cyanobacterium Anacystis nidulans," Biochemistry 1989, 28, 3057-3063.
Venkataraman, L.V., et al. "Studies on the extractability of proteins from the alga Scenedesmus acutus," 6001 Chemical abstracts, vol. 91, No. 15, Oct. 8, 1979.

* cited by examiner

*Primary Examiner* — Michael Meller
(74) *Attorney, Agent, or Firm* — Young & Thompson

(57) ABSTRACT

A process for obtaining algae extracts, includes at least the following stages:
  a) pretreatment of an algal sample,
  b) rapid heating,
  c) application of pressure that is greater than or equal to 1 bar,
  d) instantaneous expansion to a pressure that is less than or equal to 1 bar,
  and
  e) recovery of the products that are obtained in d) in liquid, solid and/or
    gaseous form. The use of algae extract products obtained by the implementation of this process is also described.

13 Claims, No Drawings

METHOD FOR OBTAINING ALGAE EXTRACTS AND USE OF THESE EXTRACTS

This invention relates to a process for treatment of algae as well as the use of extracts obtained for the implementation of this process.

Algae are living beings produced by photosynthesis whose life cycles take place in an aquatic medium. They have all the common characteristics that make it possible to identify them and to differentiate them from ground plants, but there are many kinds of them.

Aquatic algae are generally classified into two large families: prokaryotic organisms and eukaryotic organisms. They can also be classified into three categories: macroalgae, microalgae, and diatoms.

The algae cells can be bare or else covered by a complete and rigid wall, an incomplete wall, or a series of flakes, plates or strips.

The wall consists of two elements: an amorphous component, which forms the matrix, in which a fibrous component is embedded. The amorphous component primarily consists of saccharides, while the fibrous component, which forms the rigid structure of the cellular wall, generally consists of cellulose.

The algae are known and used for various properties in different fields such as human or animal food, agriculture, pharmacology, cosmetology, etc. The selection of the algae is made based on properties or desired molecules and application sectors under consideration.

Certain algae that are rich in iodine and fiber are used in weight-loss food supplements. Others have advantageous organoleptic properties and are used in food products.

It is also known that algae contain numerous compounds that are known for their beneficial health effect.

Algae have also recently been proposed as a renewable energy source (*A Look Back at the U.S. Department of Energy's Aquatic Species Program—Biodiesel from Algae*—238 pages—1998 and *Widescale Biodiesel Production from Algae*—Michael BRIGGS—August 2004). Certain kinds of algae actually produce more biomass than grains and ground oleaginous plants. They can produce lipids, sources of agrofuel fatty esters, and/or glucides, sources of bioethanol for gasolines. Furthermore, they have the advantage of not competing on the commercial and agricultural level against oleaginous plants and food grains.

This is why processes are sought that make it possible to extract molecules from the algal biomass, in particular protein, polysaccharide, or lipid fractions, but also other minor components that can be recovered, such as polyphenols, vitamins, carotenoids, etc.

However, the extraction of molecules from the algal biomass is difficult and expensive to implement, and there are several reasons for this.

Actually, with algae being greatly hydrated organisms, the current extraction processes most often involve a drying stage of the algal biomass, an operation that requires much energy and that is especially very expensive.

In addition, the unicellular composition of the algae requires a stage for breaking the cellular wall to release the different fractions that constitute them. However, this stage is difficult to implement, on the one hand, by the high inherent resistance of the cellular membrane to stresses imposed in the form of osmotic shock, temperature, microwaves and/or chemical solvent, and, on the other hand, by defense mechanisms that the living organism algae employ in response to these stresses, such as synthesis of macro sugars, membrane solidification, etc.

Finally, the algae have a very complex chemical and biochemical composition. The different families of algae compounds have a close physical and chemical interaction, and the release of these compounds, following the breaking of the cellular membrane, as well as their subsequent separation, leads to the formation of gels or stable emulsions that complicate their purification.

Furthermore, the existing processes require the use of toxic solvents or compounds of fossil origin that are harmful to the environment. By way of example, it is possible to cite the application U.S. Pat. No. 5,951,875 that describes a method for treating algae for extracting carotenoids, which uses a dissolved gas and a chemical solvent. The application GB-319333 that relates to a process for extracting pigments, salts and fatty elements of algae is also known, and said application employs petrochemical solvents that are inflammable under pressure.

In addition, it is not possible to implement the extraction of products that are obtained from an algal biomass in a press as for other materials, because the hydrated algae offer only a very low mechanical strength.

These different constraints make the processes for obtaining current algal extracts not very effective, non-profitable, and difficult to industrialize.

This is why the objective of this invention is to eliminate the drawbacks of the prior art by proposing an effective process for treating algae, which makes it possible to recover all of the products that can be recovered, which does not use toxic solvent, which prevents the risks of oxidation or denaturation of the target compounds, and which can be implemented on the industrial scale.

For this purpose, the object of the invention is a process for obtaining algae extracts, comprising at least the following stages:
a) Pretreatment of an algal sample,
b) Rapid heating of the pretreated algal sample,
c) Application of pressure that is greater than or equal to 1 bar in the product that is obtained in b),
d) Instantaneous expansion to a pressure that is less than or equal to 1 bar, and
e) Recovery of the products that are obtained in d) in liquid, solid and/or gaseous form.

The extracts that are obtained can be used in different fields based on the nature of the treated algal sample and the nature of the recovered products. They can be used in, for example, pharmaceutical, cosmetic, or food products, in agricultural or fish-farming products, or else for producing energy.

The invention is now described in detail.

The object of this invention is therefore a process for treating an algal sample that comprises at least the following stages:
a) Pretreatment,
b) Rapid heating,
c) Application of pressure that is greater than or equal to 1 bar in the product that is obtained in b),
d) Instantaneous expansion to a pressure that is less than or equal to 1 bar, and
e) Recovery of the products that are obtained in d) in liquid, solid and/or gaseous form.

Algal sample is defined as one or more alga(e) or one or more product(s) derived from algae (waste or co-products of algae), whereby algae were obtained equally well from an aquatic medium (seas, wastes of marine origin, lagoons, lakes, ponds, rivers, etc.), cultivating pools, or photo-bioreactors for algae cultivation.

Preferably, microalgae or diatoms are involved. Still more preferably, algae that belong to the family of Chlorophyceae, Cyanophyceae or Chysophyceae are involved.

Still more preferably, the algae that are used are selected from among: *Chlorella, Botryoccocus braunii, Dunaliella salina, Haematococcus pluvialis, Scenedesmus, Odontella aurita, Chondrus crispus, Porphyridium cruemtum, Spirulina platensis, Phaeodactylum tricornotum, Isochrysis* sp., *Nitzschia* sp., *Phaeodactylum tricornutum, Tetraselmis sueica*.

According to one embodiment, the algal sample is a hydrated algal biomass. The pretreatment stage a) then consists in centrifuging the sample for partially eliminating excess water.

According to another embodiment, the algal sample is a biomass that has been previously dried and/or freeze-dried. In this case, the pretreatment stage a) consists in injecting the superheated dry vapor or moist vapor into the biomass that is to be treated.

The heating temperature in stage b) is preferably between 25 and 150° C., and even more preferably between 60 and 110° C. Rapid heating is defined as heating that is carried out between 0.5 and 30 minutes.

Preferably, the heating pressure in stage c) is between 1 and 50 bar, in particular between 2 and 10 bar, and even more preferably between 4 and 6 bar. The pressure is applied during a period of between 1 and 60 minutes. It may involve autogenous pressure linked to the vaporization of water by heating algae or a rise in pressure by adding an inert gas, such as nitrogen, for example.

Likewise, the partial vacuum in stage d) is between 0.01 and 1,000 mbar, preferably between 1 and 100 mbar.

The process according to the invention can also comprise a stage that consists in adding a saline solution to the biomass before the heating stage b).

The stages b) for heating, c) for pressurization, and d) for partial vacuum can be repeated several times in succession for the purpose of further increasing the effectiveness of the process.

When the process according to the invention is implemented under the combined effect of the initial heating temperature and the instantaneous expansion, the intracellular water that is contained in the cells of the treated algal biomass is evaporated, causing a drastic increase in the osmotic pressure with the breaking of the cells as an immediate consequence. The alga(e) are then split into different fractions:

- A solid fraction that contains proteins, polysaccharides and insoluble fiber (cellulose, starch, alginate, etc.),
- A liquid fraction that contains lipids and residual water, and
- A gaseous fraction that comprises volatile compounds and condensable water vapors.

Stage e) of the process according to the invention consists in recovering these different fractions.

The gaseous products that are obtained can be recovered by condensation under cold conditions.

They can then be used as is or after treatment, in particular by purification.

In addition, the recovered water can advantageously be reused in the process according to the invention for the production of vapor.

The liquid and solid products that are obtained are separated preferably by centrifuging and/or filtration and are dried if necessary.

The liquid fraction that is recovered, or juice, has a different composition based on the nature of the treated algae sample. It can be more or less rich in lipids, sugars, or any other compound such as pigments, carotenoids, dissolved polyphenols, vitamins, etc. The liquid products that are obtained in stage e) are therefore generally treated according to techniques that are known for separating the different compounds that constitute them.

The solid fraction that is recovered after filtration is more or less rich in proteins, in polysaccharides, and in insoluble fiber and polyphenols. It can also be treated by the implementation of known techniques—so as to separate the compounds—that constitutes it.

The process according to the invention therefore makes it possible to recover all of the recoverable substances that are contained in the treated algae sample.

The recovered extracts that are obtained according to the invention can be used in particular as fuels for producing energy (bioethanol or production of eco-fuel fatty esters), as fertilizers for agriculture, as nutrients for fish farming, or else in human or animal food, pharmacology or cosmetics. Compared to existing algae extracts, they are advantageously without chemical inputs, and therefore more effective and less toxic.

Advantageously, the process for obtaining algae extract products according to the invention does not require preliminary drying of the algal sample before extraction of the target substances.

The use of a toxic solvent or a compound of fossil origin is no longer required, and the algal substances are kept intact by preventing in particular the risks of oxidation or denaturation of the products that are to be extracted.

In addition, the process according to the invention does not produce effluents, a major portion of the inputs and co-products that are used being recyclable.

According to another advantage, the process can be implemented on the industrial scale in a semi-continuous way.

The invention can be illustrated by a nonlimiting example of the process for obtaining algae extract products from *Chlorella Vulgaris*.

Stage a): A sample of microalgae of the type *Chlorella Vulgaris* is centrifuged so as to obtain a biomass that has approximately 20% dry material.

In parallel with the implementation of the process according to the invention, a portion of the centrifuged biomass is freeze-dried so as to determine its elementary composition, shown in the table below:

| Fraction | % by Weight |
| --- | --- |
| Proteins | 51 |
| Lipids | 12.5 |
| Glucides | 15.5 |
| Minerals | 7.5 |
| Insoluble Fiber | 7 |
| Water | 6.5 |

It is noted that the majority fractions of the algae *Chlorella Vulgaris* are proteins, glucides, and lipids.

Stage b): 500 g of a centrifuged *Chlorella Vulgaris* sample that titrates approximately 20% of dry material is placed in an autoclave reactor that is outfitted with a heating cover and a stirring mechanism. The chamber of the reactor is supplied with nitrogen so as to expel the residual air. While being mixed constantly, the temperature is gradually increased up to a temperature of between 80° and 100° C.

Stage c): The autogenous pressure that is linked to the vaporization that is linked to the partial evaporation of the water then tends to increase to reach a value of 3.2 bar. The heating cover is then removed.

Stage d): The chamber is then depressurized by evacuation of the water vapor and then placed quickly under a 10 mbar vacuum using a vacuum pump that is protected by a trap that is kept under cold conditions. The temperature inside the autoclave then drops quickly.

Stage e): After breaking the vacuum by the nitrogen, the mixture inside the reactor then comes in the form of a colored pasty liquid. This liquid phase is then filtered. The filtrate and the filtration cake are recovered. The gaseous phase is recovered in the vacuum trap.

The recovered liquid fraction (filtrate) corresponds to an oil-in-water mixture. It is centrifuged so as to separate water from lipids. After vacuum drying, a fatty phase is recovered that corresponds to an extraction yield of 68%. The analysis of the lipids contained in this phase is presented in the table below.

| Index/Fraction | Value |
| --- | --- |
| Acid Index | 1.3 mg of KOH/g |
| Peroxide Index | 4 meq of $O_2$/kg |
| Oleic Acid, Relative % | 22.8 |
| Linoleic Acid, Relative % | 13.8 |
| Linolenic Acid, Relative % | 29.6 |
| Palmitic Acid, Relative % | 12.2 |
| Stearic Acid, Relative % | 5.1 |
| Stearidonic Acid, Relative % | 7.8 |
| Myristic Acid, Relative % | 1.7 |
| Lauric Acid, Relative % | 0.4 |
| Arachidonic Acid, Relative % | 0.4 |

The *Chlorella Vulgaris* oil can be used as is for, for example, food or cosmetic uses or after transformation into esters in energy applications.

After filtration, the solid fraction that is recovered (solid cake) is dried in the oven.

The final mass of dry cake is 82.3 g, or an extraction yield of solid material of 85%. After analysis, it has a protein content of 60.2%, a glucide content of 17.3%, and a fiber content of 8.4%.

This recovered solid product can be used for energy purposes as is or after enzymatic digestion of fiber and sugars for producing eco-fuel bioethanol, for example. It can also be used as is as an agricultural soil conditioner or a fish-farming nutrient.

Finally, the gaseous fraction that is recovered in the vacuum trap, primarily composed of water, can be reused as a vapor source after purification.

The invention claimed is:

1. A method of making an algae extract comprising the following steps:
   a) pretreating at least one algae;
   b) heating the at least one algae to a temperature of 25-150° C. in an autoclave reactor to form a product,
   c) subjecting the product that is obtained in step b) to a pressure that is greater than or equal to 1 bar to form a second product,
   d) subjecting the second product that is obtained in step c) to a pressure that is 0.01-100 mbar to provide instantaneous expansion to form a third product, and
   e) recovering the third product that is obtained in step d) in liquid, solid and/or gaseous form to yield the algae extract,
   wherein, under the combined effect of said heating and said instantaneous expansion to a pressure that is 0.01-100 mbar, water that is contained in the cells of the algae is vaporized causing breaking of these cells and wherein said algae is selected from the group consisting of *Chlorella, Botryoccocus braunii, Dunaliella salina, Haematococcus pluvialis, Scenedesmus, Odontella aurita, Chondrus crispus, Porphyridium cruemtum, Spirulina platensis, Phaeodactylum tricornotum, Isochrysis, Nitzschia, Phaeodactylum tricornutum* and *Tetraselmis sueica*.

2. The method of making an algae extract of claim 1, wherein step a) consists of centrifuging a hydrated algal biomass.

3. The method of making an algae extract of claim 1, wherein step a) consists of injecting dry or moist vapor into a dried and/or freeze-dried algal biomass.

4. The method of making an algae extract of claim 1, wherein the pressure in step c) is between 1 and 50 bar.

5. The method of making an algae extract of claim 1, further comprising, before the heating step, a step for adding a saline solution to the algae before or after the pretreating step.

6. The method of making an algae extract of claim 1, wherein steps b), c) and d) are repeated in succession several times before step e).

7. The method of making an algae extract of claim 1, wherein the recovery of gaseous products in step e) is carried out by condensation under cold conditions.

8. The method of making an algae extract of claim 1, wherein the recovery of liquid products in step e) is carried out by separation of the liquid and solid phases by centrifuging and/or filtration.

9. The method of making an algae extract of claim 1, wherein the recovery of solid products in step e) is carried out by separation of the liquid and solid phases by centrifuging and/or filtration.

10. The method of making an algae extract of claim 1, wherein the method comprises one or more steps for treatment of the third product that is recovered in step e).

11. The method of making an algae extract of claim 1, wherein instantaneous expansion in step d) is performed at a pressure between 1 and 100 mbar.

12. The method of making an algae extract of claim 1, wherein the pressure applied in step c) is between 4 and 6 bars.

13. The method of making an algae extract of claim 1, wherein the rapidly heating in step b) is performed at a temperature between 60 and 150° C.

* * * * *